US012596034B2

(12) United States Patent
Bischoff et al.

(10) Patent No.: US 12,596,034 B2
(45) Date of Patent: Apr. 7, 2026

(54) METHOD AND SYSTEM FOR ADAPTING TO SPECIFIC TARGET PAINT APPLICATION PROCESSES

(71) Applicant: BASF Coatings GmbH, Müenster (DE)

(72) Inventors: Guido Bischoff, Muenster (DE); Carlos Vignolo, Wuerzburg (DE)

(73) Assignee: BASF COATINGS GMBH, Muenster (DE)

( * ) Notice: Subject to any disclaimer, the term of this patent is extended or adjusted under 35 U.S.C. 154(b) by 411 days.

(21) Appl. No.: 18/255,180

(22) PCT Filed: Dec. 7, 2021

(86) PCT No.: PCT/EP2021/084676
§ 371 (c)(1),
(2) Date: May 31, 2023

(87) PCT Pub. No.: WO2022/122776
PCT Pub. Date: Jun. 16, 2022

(65) Prior Publication Data
US 2024/0094057 A1     Mar. 21, 2024

(30) Foreign Application Priority Data
Dec. 12, 2020    (EP) ..................................... 20213635

(51) Int. Cl.
*G01J 3/46*        (2006.01)
*G01N 33/32*       (2006.01)
(52) U.S. Cl.
CPC .............. *G01J 3/463* (2013.01); *G01N 33/32* (2013.01); *G01J 2003/467* (2013.01)

(58) Field of Classification Search
CPC ..... G01J 3/463; G01J 2003/467; G01N 33/32
See application file for complete search history.

(56) References Cited

U.S. PATENT DOCUMENTS

| | | | | |
|---|---|---|---|---|
| 6,100,999 A | * | 8/2000 | Ikegami ................... | H04N 1/46 |
| | | | | 358/1.9 |
| 2007/0242877 A1 | * | 10/2007 | Peters .................... | G06V 10/75 |
| | | | | 382/167 |
| 2018/0080865 A1 | * | 3/2018 | Godfrey ................. | G06F 18/22 |

FOREIGN PATENT DOCUMENTS

| | | |
|---|---|---|
| EP | 2149038 B1 | 7/2018 |
| WO | 2013092679 A1 | 6/2013 |
| WO | 2016/172316 A1 | 10/2016 |

OTHER PUBLICATIONS

International Search Report and Written Opinion for corresponding PCT/EP2021/084676, mailed Apr. 2022, 11 pages.
Anonymous: "Multivariate Linear Regression : Machine Learning Medium", Aug. 23, 2017 (Aug. 23, 2017), pp. 1-6, XP055806540, Retrieved from the Internet: URL:https://machinelearningmedium.com/2017 /08/23/multivariate-linear-regression/ [retrieved on May 21, 2021] the whole document.

* cited by examiner

*Primary Examiner* — Tung S Lau
(74) *Attorney, Agent, or Firm* — Armstrong Teasdale LLP

(57)     ABSTRACT
Disclosed herein is a computer-implemented method for providing application adaption parameters to compensate for an influence of a given target paint application process on a color matching method and/or to consider an influence of a given target paint application process within a color predicting method.

13 Claims, 5 Drawing Sheets

METHOD AND SYSTEM FOR ADAPTING TO SPECIFIC TARGET PAINT APPLICATION PROCESSES

CROSS-REFERENCE TO RELATED APPLICATIONS

This application is a U.S. National Phase Application of International Patent Application No. PCT/EP2021/084676, filed Dec. 7, 2021, which claims priority to European Patent Application No. 20213635.4, filed Dec. 12, 2020, each of which is hereby incorporated by reference herein.

FIELD OF THE INVENTION

The present invention refers to a method and a system to compensate an influence of a given target paint application process on a color matching method and/or to consider an influence of a given target paint application process within a color predicting method. The present invention also refers to a respective non-transitory computer readable medium.

BACKGROUND

Most computer-aided color matching methods are based on physical models which describe an interaction of light with scattering or absorbing media, e. g. with colorants in paint layers. Each paint layer has specific light reflectance properties due to colorants contained. Each of these colorants has specific optical properties which are expressed by respective specific optical constants/specific optical data. Physical models can predict the light reflectance properties (color) of a paint layer/paint coating based on an information about the included colorants (respectively based on information about a respective formulation) together with the corresponding specific optical properties (respectively with the corresponding specific optical constants).

The specific optical constants of colorants describe e. g. the absorption and scattering properties (or the effect flake orientation) of colorants in the context of the physical model, like e. g. the K/S values in the well-known "Kubelka/Munk"-model. But the reflectance properties of a paint layer do not just only depend on the formulation. It also strongly depends on the paint application process, generally how the paint was applied to its substrate.

The specific optical properties of colorants are determined based on sample data of existing letdowns/test specimen with known formulation and known reflectance data which all were applied on a substrate by a common reference paint application process. Color predictions of a physical model as well as color matching processes are always related with this reference paint application process. The specific optical constants of the colorants include the influences of the reference paint application process to the reflectance properties of the final paint layers, respectively of the final paint coatings.

Color matching processes for a different target paint application process are subject to significant systematical errors and less accurate. Especially matches from scratch for different target paint application processes can be significantly inaccurate.

There are several methods available to apply paint onto a substrate: Some examples of paint application processes are:

Automatic or manual spraying process, different types or configurations of spray-guns in the labs or body shops, different spraying lines or drying processes in the OEM (Original Equipment Manufacturer) customer sites, drawdown method in the color development labs.

Even if the same paint (same raw material) is applied in different ways the resulting colors of paint layers (paint coatings) can strongly be influenced by the respective paint application process. Reasons for changes of the colors are:

different orientations of effect flakes in the paint layer, over-spray losses of effect flakes, particularly for big effect flakes, settling of effect flakes in the paint layer, film thickness variations of the non-hiding paint layer, tinting strength variations (shearing effects or agglomerates).

That is why it is important to use one common reference paint application process for the preparation of training data (letdowns) for the computation of optical constants of colorants, respectively of specific optical data of colorants.

For automatic paint application processes, e. g. in car production sites of the automotive industry, the color of paint depends on a type and on a configuration of a paint application process. A respective setup of the paint application process for one specific color is usually given by an OEM customer. Typically one specific color has to be applicable by a number of different spraying lines ("paint application processes"), e. g. separate spraying lines for a car body, a bumper, a side mirror and a side door. Therefore, a number of individual formulations (one for each spraying line) have to be matched to retrieve the same single target color for all requested paint application processes. In conclusion: Different formulations are matched for different paint application processes which at the end all lead to the same color. Variations within one automatic paint application process are typically small. The spraying profile of an automatic paint application process mainly depends on the spraying device (and condition) and the configuration.

For manual paint application processes, e. g. with spray-guns, the resulting color depends beside the type and the configuration of the spraying device also on the individual spraying-characteristic ("fingerprint") of the sprayer. Variations within a single paint application process are typically significantly bigger for a manual paint application process than for automatic ones. The spraying profile of a manual paint application process depends on the spraying device (and condition), the configuration and the individual spraying-characteristic ("fingerprint") of the sprayer.

Further, the color prediction accuracy of a physical model is limited. The prediction includes systematical and statistical errors. Statistical errors can be caused by the instrument or by the measurement process, e. g. variances of the position of the instrument on the sample. Systematical errors are e. g. the physical model bias and biases which are caused by differences between the respective target paint application process and the reference paint application process. That is why a new color is developed within an iterative color matching process. The matching process starts with a match from scratch or a search in a formulation database for a given target color.

The term "match from scratch" comprises a color matching method which manages without information about an existing sample coating as a first solution. This method is applied e. g. if no formulation database is available or if no adequate first solution is found in a formulation database. In practice the "match from scratch" method often starts with a pre-selection step of components which are expected to be in the target color. This pre-selection step is not mandatory. The "match from scratch" method/algorithm computes as a first solution one or more preliminary matching formulas for the target color. This/these preliminary matching formula(s) can be sprayed and/or adjusted in a following step.

In comparison to a "color adjustment method", where a sample coating as first solution is available which is used to improve the color prediction accuracy of the physical model (e. g. based on an approximation of the model error by an analysis of the "sample offset"), the accuracy of a "match from scratch" method is typically lower.

The first solution is typically not close enough to the target color. An adjustment of the first solution is applied where an offset between the predicted reflectance data and the measured reflectance data for the first solution is considered.

So the adjusted formulation is a function of the target color and the offset between the predicted reflectance data and the measured reflectance data of the first solution. If the measured reflectance data of the first solution includes a bias caused by variations within the paint application process then this error will propagate into the following formulation within the iterative color matching process.

Therefore, it is an object of the present invention to provide for a possibility to take into account a potential influence of a paint application process on a color matching method and/or on a color predicting method, in particular to compensate for this influence.

SUMMARY OF THE INVENTION

The above-mentioned object is solved by the method and the system with the features of the respective independent claims. Further embodiments are presented by the following description and the respective dependent claims.

The present disclosure refers to a method for providing application adaption parameters to compensate for an influence of a given target paint application process on a color matching method and/or on a color predicting method. Generally, both methods, the color matching process as well as the color predicting method use a database which comprises specific optical data of individual color components, the specific optical data of the individual color components being determined on the basis of known reference paint coatings with known reference color formulations and known measured reference colors, respectively, wherein the reference paint coatings are applied onto a substrate using a reference paint application process, respectively. The claimed method comprises at least the following steps:

A. applying a sample paint coating on a substrate using the given target paint application process,
B. receiving, via at least one interface of at least one computer processor, data of a color formulation of the sample paint coating,
C. retrieving, from the database, specific optical data of individual color components used in the color formulation of the sample paint coating,
D. receiving, via the at least one interface, a measured color of the sample paint coating applied on the substrate using the given target paint application process,
E. providing a numerical method and a physical model, wherein the numerical method is configured to optimize application adaption parameters by minimizing a given cost function starting from a given set of initial application adaption parameters, the given cost function being particularly chosen as a color distance between the measured color and a predicted color of the sample paint coating, and the physical model is configured to predict the color of the sample paint coating by using as input parameters the color formulation of the sample paint coating and the retrieved specific optical data of the individual color components used in the color formulation of the sample paint coating and respective preliminary application adaption parameters resulting in the course of optimization,
F. calculating, using the at least one computer processor and using the numerical method and the physical model implemented and running on the at least one computer processor, the application adaption parameters by comparing the recursively predicted color of the sample paint coating with the measured color of the sample paint coating until the given cost function falls below a given threshold.

The proposed method is at least partly computer-implemented.

The terms "specific optical data of individual color components", "specific optical data of the individual color components" or "specific optical data of the colorants" are used synonymously herein and comprise specific optical properties and specific optical constants of the respective individual color components, i.e. colorants. The individual color components used in the color formulations of the paint coating are selected from the group comprising at least: color pigments, i.e. so-called solid pigments, effect pigments, binders, solvents and additives, such as matting pastes. The terms "formulation", "color formulation" and "paint formulation" are used synonymously herein. The terms "processor" and "computer processor" are used synonymously herein.

Known approaches for color formulation calculation on the basis of a radiative transfer model can be found in the literature, reference is made, for example, to "Farbenphysik für industrielle Anwendungen" of Georg A. Klein.

A basic idea of the color formulation calculation is a characterization of the specific optical data, i.e. the optical properties and/or the optical constants of all relevant individual color components, e.g. of all color pastes/colorants, on the basis of previously calibration coatings, i.e. on the basis of respective measurements of such calibration coatings. These calibration coatings correspond to existing letdowns with known formulation and known reflectance data, respectively, which all were applied by the common reference paint application process. Color predictions, using the physical model, as well as color matching processes are always related with this reference paint application process. The specific optical constants of the colorants include the influence of the reference paint application process to the predicted reflectance properties of the respective final paint coatings/layers.

Starting with the given set of initial application adaption parameters, the optimized application adaption parameters are calculated iteratively, i.e. via a series of intermediate preliminary application adaption parameters. The initial application adaption parameters are neutral parameters. That means that use of the initial application adaption parameters yields to color predictions which are equal to those using the reference paint application process.

According to the present invention, the physical model for the prediction of the reflectance properties of a paint coating (related with the reference paint application process), i.e. for the prediction of the color of the paint coating is extended with an additional application adaption module: The additional application adaption module works in interaction with the physical model and is configured to adapt the predicted reflectance data to a specific target paint application process. The additional module is configurable by input of the target application adaption parameters which may be calculated according to step F. of the method as described before. These application adaption parameters describe differences between the target paint application process in comparison to the respective reference paint application process. Examples for application adaption parameters are:

Paint layer thickness adaption: more/less thick (Applicable for non-hiding paint layers; adjust the hiding power of a paint layer)

Effect flake orientation adaption: better/worse flake orientation (Applicable for effect colors; adjust the lightness-/color-flop behavior of a paint layer)

Effectivity of solid colorants: more/less effective (Adjust the tinting strength differences of solid colorants which could be cause e. g. by shearing effects or by agglomerates)

Effectivity of effect colorants: more/less effective (Adjust differences of the reflection power of effect colorants which could be caused by over-spray losses or settling or leaving effects)

By means of the proposed method, the application adaption parameters for a given target paint application process can be determined implicitly based on an analysis of existing sample coating(s) (e. g. one or more existing tinting step(s) of a color matching process) which are applied with the given target paint application process. Also a list of existing sample coatings from a database (which are related with the given target paint application process, particularly with an individual human sprayer) could be used for the determination of the respective target application adaption parameters.

According to one embodiment of the proposed method, the method is executed for a plurality of different given target paint application processes wherein the respective application adaption parameters calculated for a respective one of the plurality of different given target paint application processes are retrievably stored in a repository and assigned to the respective one of the plurality of different given target paint application processes as process-specific application adaption parameters. These process-specific application adaption parameters can then be called from the repository at any time on request.

The provision of the process-specific application adaption parameters allows the color matching and adjustment processes to be carried out for any specific given target paint application process whose assigned target application adaption parameters are stored in the repository.

As mentioned above, the application adaption parameters may each be classified into a classification system and subsumed therein under a generic term, such as "paint layer thickness adaption", "effect flake orientation adaption" etc. Each application adaption parameter takes a specific value for a particular target paint application process. Accordingly, a matrix A can be created with matrix elements a $a_{i,j}$ in which the respective generic terms, under which the respective application adaption parameters can be subsumed, are assigned to respective columns i and the target paint application processes to respective rows j, or vice versa, so that the respective values that the respective application adaption parameters take up for a respective target paint application process can be stored and retrieved exactly in a matrix element $a_{i,j}$. Table 1 shows a simplified example for only one target paint application process wherein each application adaption parameter, Adaption Parameter$_1$, Adaption Parameter$_2$, Adaption Parameter$_3$, ..., Adaption Parameter$_n$, takes a process specific value, Value$_1$ Value$_2$, Value3, ..., Value$_n$, respectively.

TABLE 1

| Application adaption parameters | |
| --- | --- |
| Adaption Parameter$_1$ | Value$_1$ |
| Adaption Parameter$_2$ | Value$_2$ |
| Adaption Parameter$_3$ | Value$_3$ |
| ... | ... |
| Adaption Parameter$_n$ | Value$_n$ |

According to still a further embodiment of the proposed method, the given target paint application process is selected from a group of available paint application processes, wherein each of the available paint application processes is assigned a set of process-specific application adaption parameters wherein each application adaption parameter takes into account a respective variable which changes with the respective paint application process in relation to the reference paint application process and wherein each application adaption parameter takes on a process-specific value for each of the available paint application processes.

As already mentioned above, each application adaption parameter is assigned to an adaption measure of a number of different adaption measures, the number of different adaption measures comprising at least one of: layer thickness adaption, adaption of effect flake orientation distribution, adaption of effectivity of solid color components, adaption of effectivity of effect color components.

A second aspect of the present invention refers to a computer-implemented color matching method using a paint color formulation calculation algorithm running on a processor and a database which comprises specific optical data of individual color components, the specific optical data of the individual color components being determined on the basis of known reference paint coatings with known reference color formulations and known measured reference colors, respectively, wherein the reference paint coatings are applied onto a substrate using a reference paint application process, respectively. The proposed color matching method is aimed at determining a target color formulation for a target paint coating which matches a given target color when being applied on a substrate using a given target paint application process, the method comprising:

receiving, via at least one interface, the given target color, receiving, via the at least one interface, (target) application adaption parameters which are manually input, retrieved from a repository and/or calculated using a method as described herein, calculating, using the given target color and the received application adaption parameters as input parameters for the paint color formulation calculation algorithm, a color formulation with optimized concentrations of individual color components as target color formulation for the target paint coating when the target paint coating is applied on a substrate using the given target paint application process.

The paint color formulation calculation algorithm uses numerical methods that optimize the concentrations of all available color components by minimizing a given cost function (such as a color distance between the target coating and a theoretically predicted color of a respective formulation) under consideration of the received target application adaption parameters.

Each numerical method comprises a number of successive approximation steps. In each approximation step, a preliminary paint coating is assumend/provided and fed into the physical model in order to predict its respective reflectance data which are then compared, using the cost function, with the reflectance data (target color) of the target paint coating.

In a preferred embodiment, the paint color formulation calculation algorithm is realised by a numerical method and a physical model, wherein the numerical method is configured to optimize concentrations of individual color components of a preliminary color formulation in relation to the target color by minimizing a given cost function, starting from a given initial color formulation, the given cost function being particularly chosen as a color distance between the received target color and a predicted color of the preliminary color formulation, and the physical model is configured to predict the color of the preliminary color formulation by using as input parameters concentrations of the individual color components used in the preliminary color formulation, specific optical data of the individual color components used in the color formulation and the received application adaption parameters, and wherein the optimized concentrations of the color components are calculated by comparing the recursively predicted color of the preliminary color formulation with the target color until the given cost function falls below a given threshold.

A third aspect of the present invention refers to a computer-implemented method for predicting reflectance data of a target paint coating wherein the target paint coating is to be applied on a substrate using a given target paint application process. The proposed method uses a color predicting physical model running on a processor, and a database which comprises specific optical data of individual color components, the specific optical data of the individual color components being determined on the basis of known reference paint coatings with known reference color formulations and known measured reference colors, respectively, wherein the reference paint coatings are applied onto a substrate using a reference paint application process, respectively. The method comprises at least the following steps:

a. receiving, via at least one interface, data of a color formulation of the target paint coating, b. retrieving, from the database, specific optical data of individual color components used in the color formulation of the target paint coating, c. receiving, via the at least one interface, (target) application adaption parameters which are manually input, retrieved from a repository and/or calculated using a method as described herein, d. calculating the reflectance data of the target paint coating using the physical model implemented and running on the processor, wherein the received data of the color formulation of the target paint coating, the retrieved specific optical data of the individual color components used in the color formulation and the received target application adaption parameters are entered into the model as input parameters, and making the predicated reflectance data of the target paint coating available in the processor for further use in paint formulation calculation and/or for the development of automotive coatings and/or automotive refinish coatings.

As already mentioned before, according to the present invention, the physical model for the prediction of the reflectance properties of a paint coating (related with the reference paint application process), i.e. for the prediction of the color of the paint coating is extended with the additional application adaption module: The additional application adaption module works in interaction with the physical model and is configured to adapt the predicted reflectance data to the given target paint application process. The additional module is configurable by input of the (target) application adaption parameters.

A fourth aspect of the present invention refers to a computer-implemented method for color simulation for an available paint application process, using a color simulation algorithm running on a processor, and a database which comprises specific optical data of individual color components, the specific optical data of the individual color components being determined on the basis of known reference paint coatings with known reference color formulations and known measured reference colors, respectively, wherein the reference paint coatings are applied onto a substrate using a reference paint application process, respectively. The simulation method aims at determining whether a given target color of a target paint coating is producible with the available paint application process, the method comprises at least:

receiving, via at least one interface, the given target color, retrieving, from the database, specific optical data of individual color components used in a color formulation of the target paint coating, receiving, via the at least one interface, application adaption parameters for the available paint application process which are manually input, retrieved from a repository and/or calculated using a method as described herein, calculating, using the retrieved specific optical data of the individual color components used in the color formulation of the target paint coating and the received application adaption parameters as input parameters for the color simulation algorithm, a color formulation with optimized concentrations of the individual color components with respect to the target color, and predicting a color associated with the calculated color formulation when a respective paint coating of the calculated color formulation is applied on a substrate using the available paint application process, comparing the predicted color with the target color, particularly by determining a color distance, and indicating that the target color is producible with the available paint application process if a difference, particularly if the color distance, between the predicted color and the target color is within a given tolerance range.

The present invention also refers to a system, comprising at least:

a database which comprises individual color components, such as pigments and/or pigment classes, and specific optical data associated with the respective individual color components, the specific optical data of the individual color components being determined on the basis of known reference paint coatings with known reference color formulations and known measured reference colors, the reference paint coatings being applied to a substrate using a reference paint application process, respectively, at least one computer processor, which is in communicative connection with the database, and programmed to execute the method according to any one of the preceding claims.

The system may further comprise an input device that is configured to receive, via an appropriate interface, such as USB, an input of data. Such input device can be a computer keyboard, a microphone, a video camera, a data carrier or any combination thereof. The system may further comprise an output device that is configured to output, and in particular to display, the respective results calculated by carrying out one of the above methods. The output device is one of the group comprising at least: acoustic device, haptic device, display device and any combination thereof. The output device is in a communicative connection, via a respective interface, with the at least one computer processor.

Furthermore, the present invention refers to a non-transitory computer readable medium with a computer program with program codes that are configured and programmed, when the computer program is loaded and executed by at least one computer processor which is in communicative connection with a database which comprises individual color components, such as pigments and/or pigment classes, and specific optical data associated with the respective individual color components, the specific optical data of the individual color components being determined on the basis of known reference paint coatings with known reference color formulations and known measured reference colors, the reference paint coatings being applied onto a substrate using a reference paint application process, respectively, to execute any one of the methods as described herein.

Each of the communicative connections between the different components may be a direct connection or an indirect connection, respectively. Each communicative connection may be a wired or a wireless connection. Each suitable communication technology may be used. The database and the at least one computer processor, each may include one or more communications interfaces for communicating with each other. Such communication may be executed using a wired data transmission protocol, such as fiber distributed data interface (FDDI), digital subscriber line (DSL), Ethernet, asynchronous transfer mode (ATM), or any other wired transmission protocol. Alternatively, the communication may be wirelessly via wireless communication networks using any of a variety of protocols, such as General Packet Radio Service (GPRS), Universal Mobile Telecommunications System (UMTS), Code Division Multiple Access (CDMA), Long Term Evolution (LTE), wireless Universal Serial Bus (USB), and/or any other wireless protocol. The respective communication may be a combination of a wireless and a wired communication.

The computer-readable medium suitable for storing the computer program instructions (i.e. program codes) and data include all forms of non-volatile memory and memory devices, including by way of example semiconductor memory devices, such as erasable programmable read-only memory (EPROM), electrically-erasable programmable read-only memory (EEPROM), and flash memory devices; magnetic disks, such as, internal hard disks or removable disks; magneto-optical disks; optical disks; and CD-ROM, DVD+R, DVD-R. DVD-RAM, and DVD-ROM disks or a combination of one or more of them. Such a memory device may store various objects or data, including caches, classes, applications, backup data, jobs, web pages, web page templates, database tables, repositories storing dynamic information, and any other appropriate information including any parameters, variables, algorithms, instructions, rules, constraints, and/or references thereto. Additionally, the memory may include any other appropriate data, such as policies, logs, security or access data, reporting files, as well as others. The computer processor and the memory can be supplemented by, or incorporated in, special purpose logic circuitry.

The computer program instructions can be a program software, a software application, a module, a software module, a script, or code, and can be written in any form of programming language, including compiled or interpreted languages, or declarative or procedural languages, and can be deployed in any form, including as a stand-alone program or as a module, component, subroutine, or other unit suitable for use in a computing environment. In one embodiment, the computer-executable instructions (i.e. program codes) of the present disclosure are written in HTML, TS (TypeScript), and CSS (Cascading Style Sheets).

A computer program may, but need not, correspond to a file in a respective file system. A computer program can be stored in a portion of a file that holds other programs or data, e.g., one or more scripts stored in a markup language document, in a single file dedicated to the computer program in question, or in a plurality of coordinated files, e.g., files that store one or more modules, sub-programs, or portions of code. A computer program can be deployed to be executed on one computer or on a plurality of computers that are located at one site or distributed across a plurality of sites and interconnected by a communication network. Portions of the computer programs may be designed as individual modules that implement the various features and functionality through various objects, methods, or other processes. Alternatively, the computer programs may instead include a number of sub-modules, third-party services, components, libraries, and such, as appropriate. Conversely, the features and functionality of various components can be combined into single components as appropriate.

Systems suitable for the execution of the method of the present disclosure can be based on general or special purpose microprocessors, both, or any other kind of CPU. Generally, a CPU will receive instructions and data from a read-only memory (ROM) or a random access memory (RAM) or both. Essential elements of the system are a CPU for performing or executing instructions (i.e. program codes) and one or more memory devices (such as the database) for storing instructions (i.e. program codes) and data. Generally, the system includes, or is operatively coupled to at least one memory device and is configured to receive data from or transfer data to, or both, one or more memory devices for storing data, The at least one memory device may comprise, e.g., magnetic disks, magneto-optical disks, or optical disks. However, the system need not have such memory devices. Moreover, the system can be embedded in another device, e.g., a mobile telephone, a personal digital assistant (PDA), or a portable storage device, e.g., a universal serial bus (USB) flash drive, to name just a few.

One main aspect for the application adaption method as described herein was an adaption of existing color matching and adjustment methods individually to specific customer's target paint application processes, e. g. to specific OEM customer's reference paint application processes. It allows considering specific characteristics (like e. g. special lightness- or color-flop characteristics of effect pigments in paint) already in a first match. Matches from scratch can be closer to a given target color. The color matching process can converge faster. Lab-effort for color development and for customer service matching can be reduced.

Further potential use cases for the new developed application adaption method are:
  Data analysis of existing colors which were sprayed by a specific paint application process, respectively by an individual sprayer; Generation of calibration data, respectively a spraying profile of an individual sprayer: The calibration data/spraying profile can be used as target application adaption parameters in order to optimize formulations for the corresponding paint application process; this will directly improve the current color development process as well as future color matches.

Data analysis of existing colors with respect to statistical and systematical application process variations within the color development process: An aim is to extract information about the repeatability of the paint application process; this information can help to improve the color development process and/or to derive criteria about the end-point of a color adjustment process, respectively how far a following color adjustment step makes sense.

The following description is presented and is provided in the context of one or more particular implementations. Various modifications to the disclosed implementations will be readily apparent to a person skilled in the art, and the general principles defined herein may be applied to other implementations and applications without departing from the scope of the disclosure.

Implementations of the subject matter and the functional operations described in this disclosure can be implemented in digital electronic circuitry, in tangibly-embodied computer software, in computer hardware, including the structures disclosed in this disclosure and their structural equivalents, or in combinations of one or more of them. Implementations of the subject matter described in this disclosure can be implemented as one or more computer programs, i.e., one or more modules of computer program instructions encoded on a tangible, non-transitory computer-readable medium for execution by the at least one computer processor. Alternatively or in addition, the computer program instructions can be encoded on an artificially-generated propagated signal, e.g., a machine-generated electrical, optical, or electromagnetic signal that is generated to encode information for transmission to a suitable receiver device for execution by at least one computer processor. The computer-storage medium can be a machine-readable storage device, a machine-readable storage substrate, a random or serial access memory device, or a combination of one or more of them.

The details of one or more implementations of the subject matter of this disclosure are set forth in the accompanying drawings and the description.

Other features, aspects, and advantages of the subject matter will become apparent from the description, the drawings, and the claims.

DETAILED DESCRIPTION OF THE DRAWINGS

Identical units or components are provided with identical reference signs across all figures.

Figure 1:
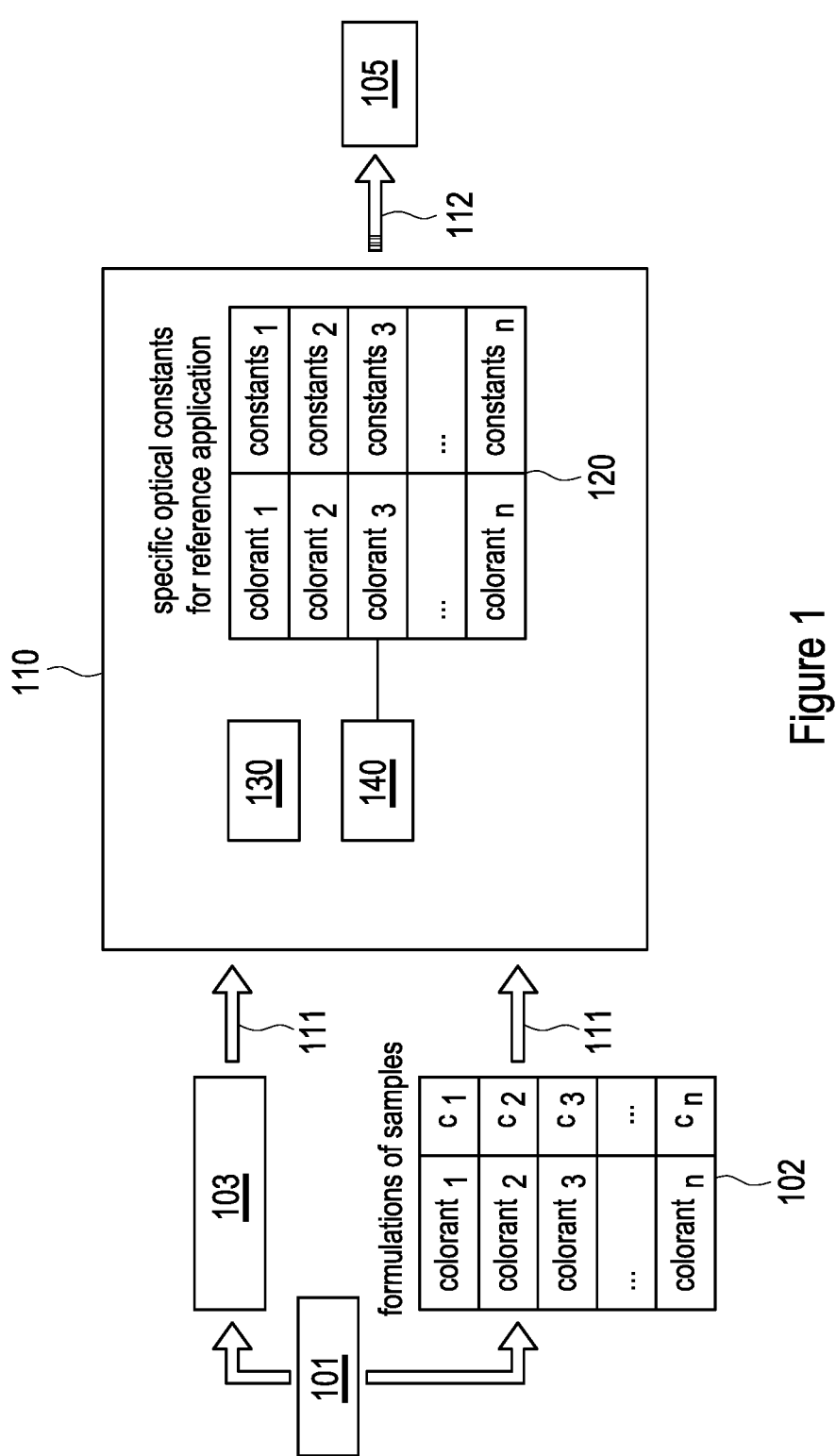
FIG. 1 shows a schematic block diagram that illustrates an embodiment of a method for providing application adaption parameters according to the present invention.
Figure 2:
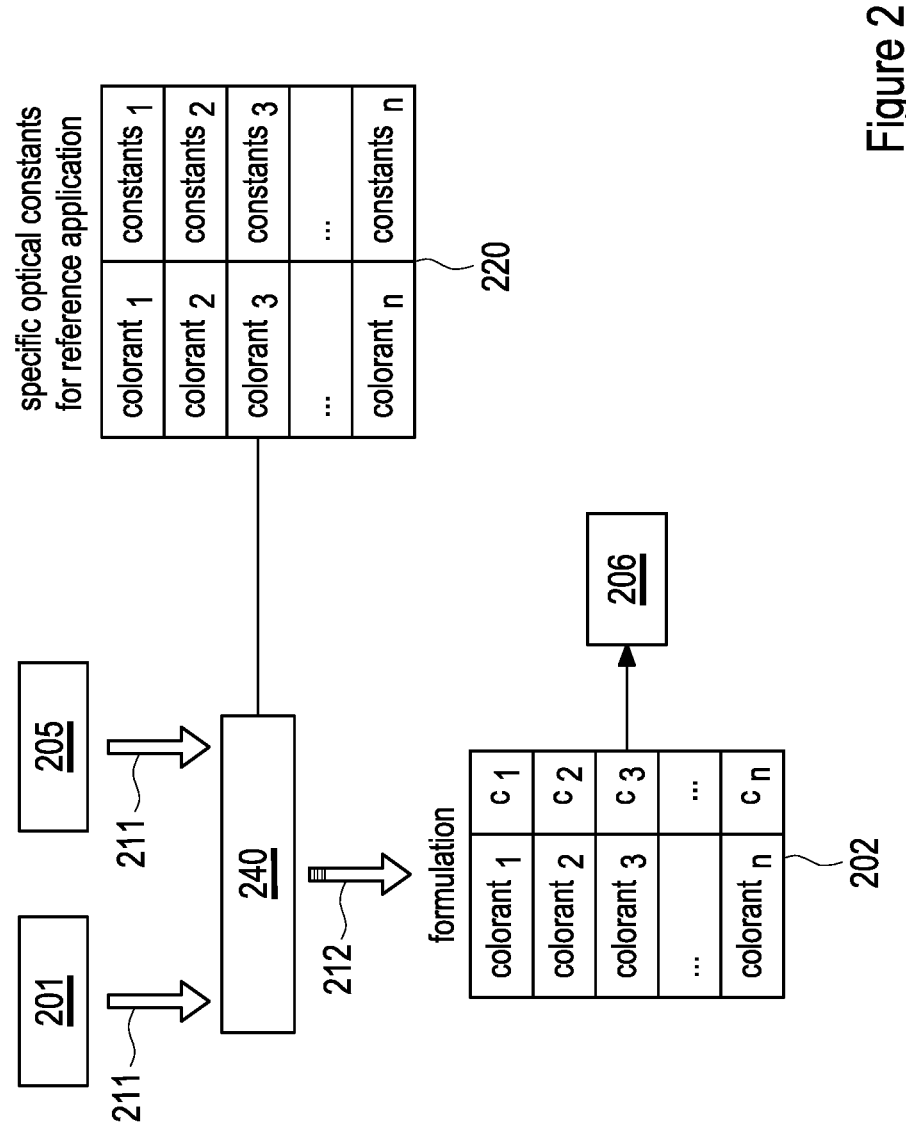
FIG. 2 shows a schematic block diagram that illustrates an embodiment of a method for color matching according to the present invention.
Figure 3:
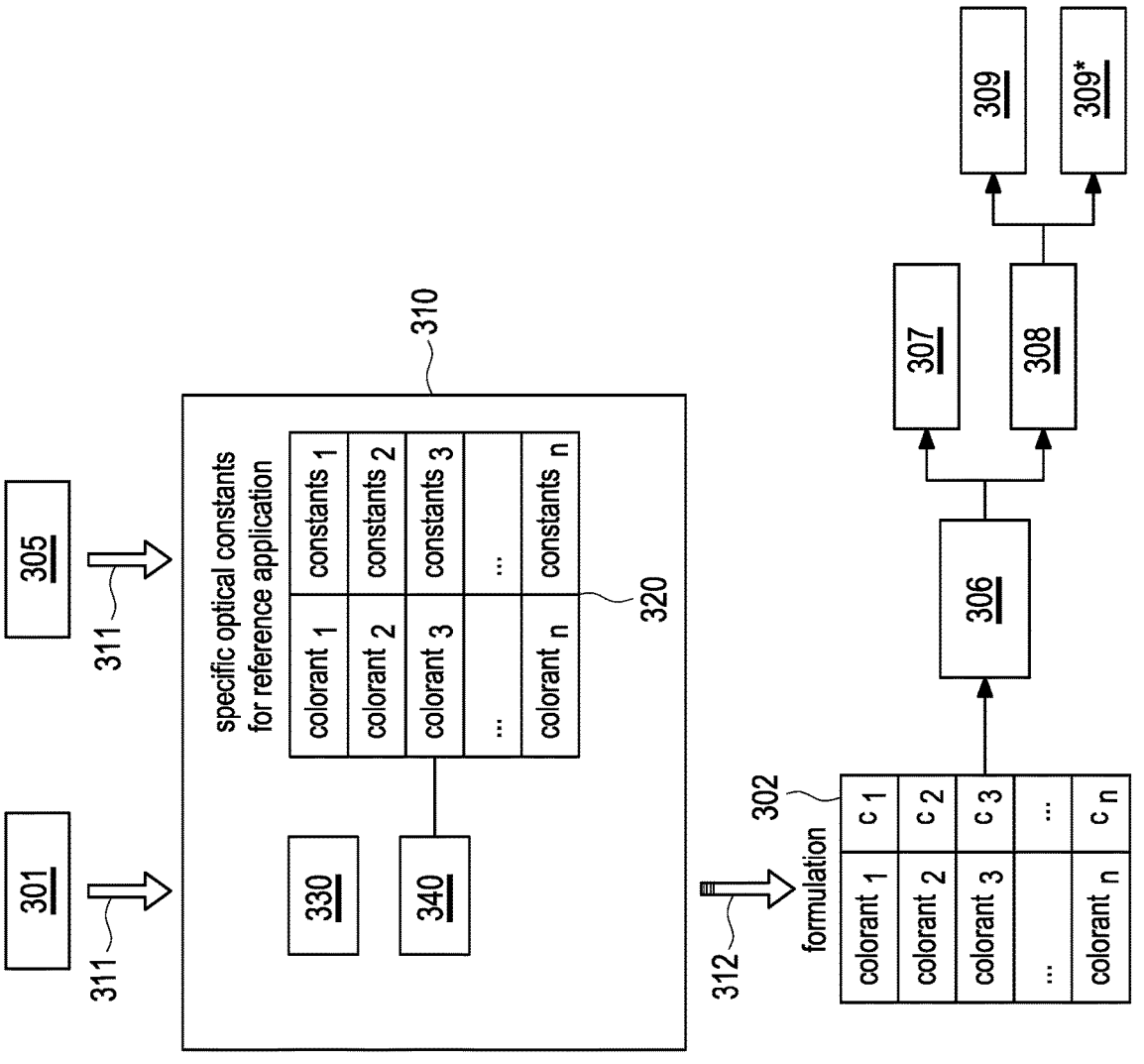
FIG. 3 shows a schematic block diagram that illustrates another embodiment of a method for color matching according to the present invention.
Figure 4:
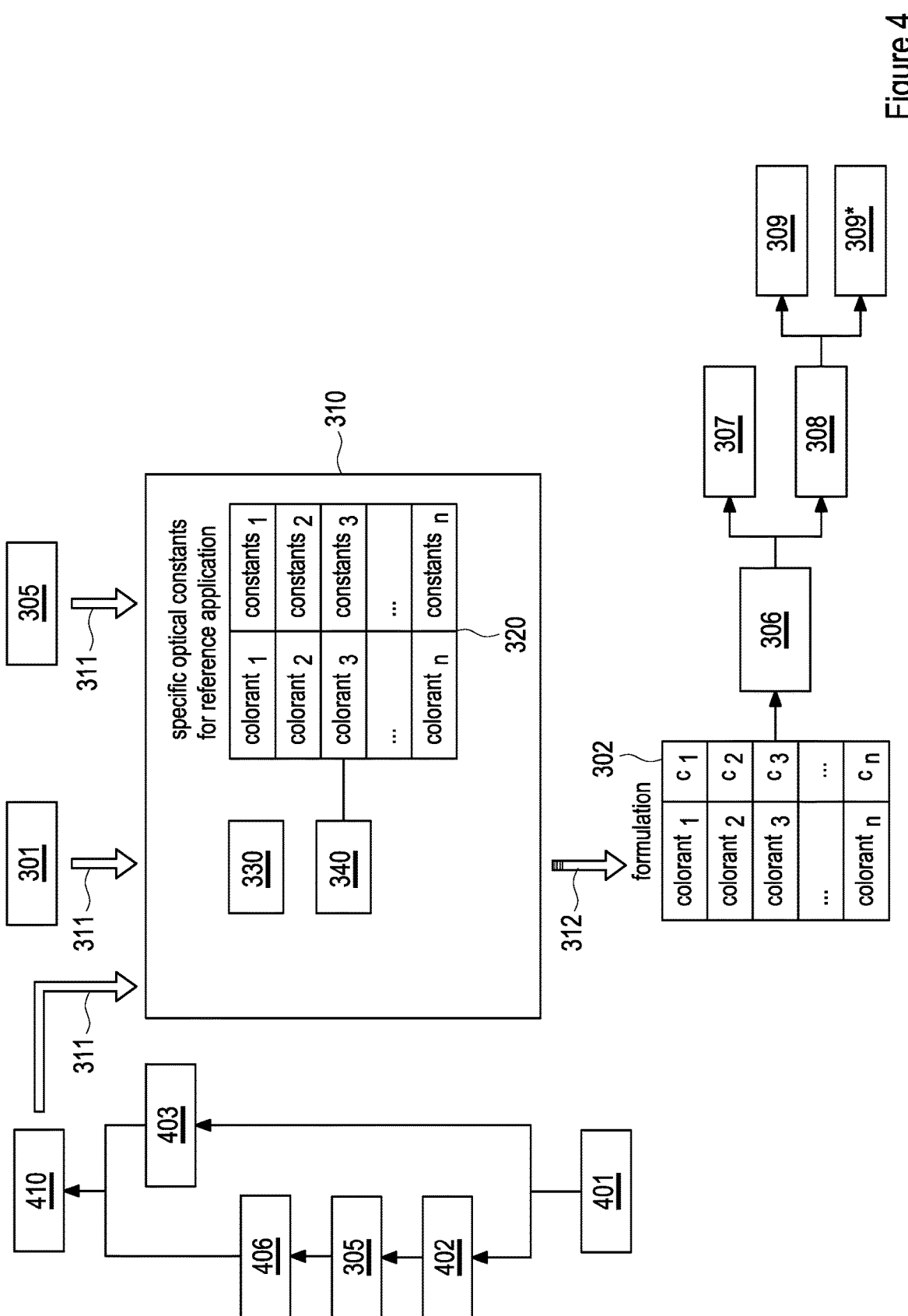
FIG. 4 shows a schematic block diagram that illustrates an embodiment of a method for color adjustment according to the present invention.

FIG. 1 shows an embodiment of a system according to the present invention. The system comprises a computer processor 110 and a database 120. The database 120 comprises individual color components, $colorant_1$, $colorant_2$, $colorant_3$, . . . , $colorant_n$, such as pigments and/or pigment classes, and specific optical data, $constants_1$, $constants_2$, $constants_3$, . . . , $constants_n$, associated with the respective individual color components, the specific optical data of the individual color components being determined on the basis of known reference paint coatings with known reference color formulations and known measured reference colors, the reference paint coatings being applied onto a substrate using a reference paint application process, respectively. The computer processor 110 is in communicative connection with the database 120, and programmed to execute an embodiment of the method for providing application adaption parameters as described herein. Such application adaption parameters serve to compensate for an influence of a given target paint application process on a color matching method and/or to consider an influence of a given target paint application process within a color predicting method.

The application adaption parameters can be computed based on data of existing tinting steps, respectively of existing sample paint coatings 101.

These sample paint coatings 101 are applied on a substrate using the given target paint application process. The respective colors 103 of the sample paint coatings 101 are measured. Data of the respective color formulations 102 of the respective sample paint coatings are provided. A respective color formulation 102 specifies all included colorants, $colorant_1$, $colorant_2$, $colorant_3$, . . . $colorant_n$ with their respective concentrations, $c_1$, $c_2$, $c_3$, . . . , $c_n$.

The data of the color formulations 102 of the sample paint coatings 101 are received via at least one interface 111 of the computer processor 110. Furthermore, the measured colors 103 of the sample paint coatings 101 are received via the at least one interface 111 of the computer processor 110.

A numerical method 130 and a physical model 140 are provided and implemented on the computer processor 110. The numerical method 130 is configured to optimize application adaption parameters by minimizing a given cost function starting from a given set of initial application adaption parameters.

The initial application adaption parameters are neutral parameters. That means that use of the initial application adaption parameters yields to color predictions which are equal to those using the reference paint application process. The given cost function is chosen as a color distance between the measured color 103 of a respective one of the existing sample paint coatings 101 and a predicted color of the respective sample paint coating. The physical model is configured to predict the color of the respective sample paint coating by using as input parameters the color formulation 102 of the respective sample paint coating, specific optical data of the individual color components used in the color formulation 102 of the respective sample paint coating, and respective preliminary application adaption parameters resulting in the course of optimization. The specific optical data are retrieved from the database 120. As already mentioned before, the specific optical properties of colorants are determined based on data of existing letdowns/test specimen with known formulation and known reflectance data which all were applied on a substrate by the common reference paint application process. Therefore, color predictions of the physical model are related with this reference paint application method. The specific optical constants/data of the colorants include the influences of the reference paint application process to the reflectance properties of the final paint layers.

By using the computer processor 110 and using the numerical method 130 and the physical model 140 implemented and running on the computer processor 110, the application adaption parameters 105 are calculated by comparing for the sample paint coatings, the recursively predicted color of a respective one of the sample paint coatings with the measured color 103 of the respective one sample paint coating until the given cost function falls below a given threshold.

The calculated optimized application adaption parameters 105 are made available and optionally output via a further interface 112 on an output device such as a display. These calculated optimized application adaption parameters 105 are characteristic for the one specific target paint application process. The method may executed for a plurality of different given target paint application processes wherein the respective application adaption parameters calculated for a respective one of the plurality of different given target paint application processes may then be retrievably stored in a repository and assigned to the respective one of the plurality of different given target paint application processes as process-specific application adaption parameters. These process-specific application adaption parameters can then be retrieved from the repository at any time on request.

A matching process starts with a match from scratch or a search in a formulation database for a given target color 201.

Color predictions of a physical model 240 are always related with a reference paint application process because the physical model 240 uses the database 220 as a basis for the color prediction. The database 220 comprises individual color components, $colorant_1$, $colorant_2$, $colorant_3$, . . . , $colorant_n$ such as pigments and/or pigment classes, and specific optical data, $constants_1$, $constants_2$, $constants_3$, . . . , $constants_n$, associated with the respective individual color components. The specific optical properties of colorants are determined based on data of existing letdowns/test specimen with known formulation and known reflectance data which all were applied on a substrate by a common reference paint application process. The specific optical constants of the colorants include the influences of the reference paint application process to the reflectance properties of the final paint layers. However, if you are looking for a formulation 202 of a paint coating whose color matches the target color 201 wherein the paint coating is to be applied on a substrate using a target paint application process other than the reference paint application process, the characteristic of the target paint application process compared to the reference paint application process must be taken into account.

Therefore, the prediction of the color of the paint coating to be found, using the physical model 240, is extended with an additional application adaption module:

The additional application adaption module works in interaction with the physical model 240 and is configured to adapt the predicted reflectance data to the target paint application process. The additional module is configurable by input of target application adaption parameters 205 which are calculated as exemplarily described in FIG. 1. These application adaption parameters 205 describe differences between the target paint application process in comparison to the respective reference paint application process. Examples for application adaption parameters are:

Paint layer thickness adaption: more/less thick
(Applicable for non-hiding paint layers; adjust the hiding power of a paint layer)

Effect flake orientation adaption: better/worse flake orientation
(Applicable for effect colors; adjust the lightness-/color-flop behavior of a paint layer)

Effectivity of solid colorants: more/less effective
(Adjust the tinting strength differences of solid colorants which could be caused e. g. by shearing effects or by agglomerates)

Effectivity of effect colorants: more/less effective
(Adjust differences of the reflection power of effect colorants which could be caused by over-spray losses or settling or leaving effects)

The target color 201 and the target application adaption parameters 205 are received by the physical model 240 which is implemented and running on a computer processor, via an interface 211. In order to determine the formulation 202 for a paint coating whose color matches the target color 201 when being applied on a substrate using the target paint application process, the physical model 240 calculates, using the target color 201, the target application adaption parameters 205 and the specific optical constants of the available colorants from the database 220, an optimized formulation 202 which specifies all included colorants, $colorant_1$, $colorant_2$, $colorant_3$, . . . $colorant_n$ with their respective concentrations, $c_1$, $c_2$, $c_3$, . . . , $c_n$. This formulation 202 and its predicted color 206 when being applied using the target paint application process, can be output via an interface 212 on an output device.

A matching process starts with a match from scratch or a search in a formulation database for a given target color 301.

The first solution is typically not close enough to the target color 301. Therefore, the physical model 340 is used in combination with a numerical method, i.e. a numerical optimization algorithm 330 to obtain an optimised formulation 302 by iteration. The physical model 340 uses again the database 320 as a basis for the color prediction. The database 320 comprises individual color components, $colorant_1$, $colorant_2$, $colorant_3$, . . . , $colorant_n$, such as pigments and/or pigment classes, and specific optical data, $constants_1$, $constants_2$, $constants_3$, . . . , $constants_n$, associated with the respective individual color components. The specific optical properties of colorants are determined based on data of existing letdowns/test specimen with known formulation and known reflectance data which all were applied on a substrate by a common reference paint application process. However, if you are looking for a formulation 302 of a paint coating whose color matches the target target color 301 wherein the paint coating is to be applied on a substrate using a target paint application process other than the reference paint application process, the characteristic of the target paint application process compared to the reference paint application process are taken into account by providing target application adaption parameters 305 which are calculated as exemplarily described in FIG. 1.

The target color 301 and the target application adaption parameters 305 are received by the computer processor 310, on which the physical model 340 and the numerical optimization algorithm 330 are implemented and running, via an interface 311. In order to determine the formulation 302 for a paint coating whose color matches the target color 301 when being applied on a substrate using the target paint application process, the target color 301, the target application adaption parameters 305 and the specific optical constants of the available colorants from the database 320 are used and an optimized formulation 302 is iteratively determined. The formulation 302 specifies all included colorants, $colorant_1$, $colorant_2$, $colorant_3$, . . . $colorant_n$ with their respective concentrations, $c_1, c_2, c_3, \ldots, c_n$. This formulation 302 and its predicted color 306 when being applied using the target paint application process, can be output via an interface 312 on an output device. The predicted color 306 is composed of a true color 307 of the optimized formulation 302 when being applied on a substrate using the target paint application process, and a systematical bias 308 which corresponds to a model bias 309. Due to the inclusion of the target application adaption parameters 305 in the calculation, there is no paint application process bias 309*.

A matching process starts with a match from scratch or a search in a formulation database for the given target color 301.

As already indicated before, a first solution 401 is typically not close enough to the target color 301. An adjustment of the first solution 401 is applied where an offset 410 between the predicted reflectance data, i.e. the predicted color 406 and the measured reflectance data 403 for the first solution 401 is considered.

So the adjusted formulation is a function of the target color 301 and the offset 410 between the predicted reflectance data 406 and the measured reflectance data 403 of the first solution 401. If the measured reflectance data 403 of the first solution 401 includes a bias caused by variations within the paint application process then this error will propagate into the following formulation within the iterative color matching process.

Therefore, it is proposed to avoid such paint application process bias 309* by taking into account the diversity of the paint application processes already in the first iteration step, i.e. when considering the first solution 401.

The offset 410 which is independent of the paint application process is calculated on the basis of the first solution 401. A color formulation 402 of the first solution 401 is known. The first solution 401 is applied as paint coating on a substrate using the target paint application process and its color is measured. The measured color 403 of the first solution 401 is provided. Furthermore, the physical model 340 is used to predict the color of the first solution 401 on the basis of the known formulation 402. As the physical model 340 uses the database 320 and is, thus, related to the reference paint application process, the target paint application process is taken into account by combining the physical model 340 with the target application adaption parameters 305. The predicted color 406 of the first solution 401 is now predicted on the assumption that the underlying formulation 402 is applied as paint coating on a substrate using the target paint application process. Therefore, both the measured color 403 and the predicted color 406 refer to the same target paint application process. The offset 410 as difference between the measured color 403 and the predicted color 406 is, therefore, independent of the underlying target paint application process. This offset 410 can now be used for the iterative adjustment process and is provided as further input parameter via the interface 311 to the physical model 340.

Figure 5:
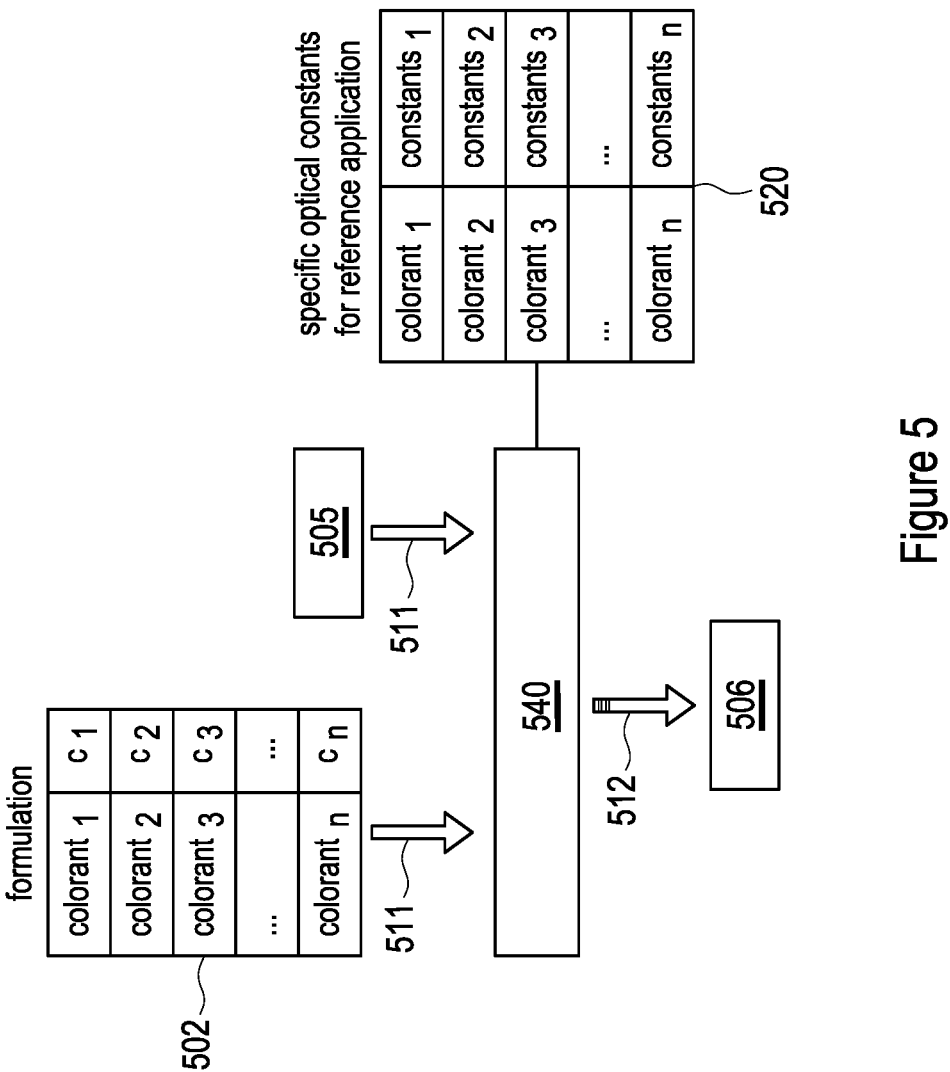
FIG. 5 shows a schematic block diagram that illustrates an embodiment of a method for color simulation according to the present invention.

FIG. 5 illustrates schematically an embodiment of a computer-implemented method for predicting reflectance data of a target paint coating according to the present invention. The target paint coating is to be applied on a substrate using a given target paint application process. The proposed method uses a color predicting model, i.e. a physical model 540 (as already described in connection with the above figures) which is running on a computer processor, and a database 520 (as already described in connection with the above figures) which comprises individual color components, colorant$_1$, colorant$_2$, colorant$_3$, . . . , colorant$_n$, such as pigments and/or pigment classes, and specific optical data, constants$_1$, constants$_2$, constants$_3$, . . . , constants$_n$, associated with the respective individual color components, the specific optical data of the individual color components being determined on the basis of known reference paint coatings with known reference color formulations and known measured reference colors, respectively, wherein the reference paint coatings are applied onto a substrate using a reference paint application process, respectively.

According to the proposed method, data of a color formulation 502 of the target paint coating are received by the computer processor via at least one interface 511. Specific optical data of individual color components used in the color formulation 502 of the target paint coating are retrieved from the database 520. The formulation 502 specifies all included colorants, colorant$_1$, colorant$_2$, colorant$_3$, . . . colorant$_n$ with their respective concentrations, $c_1, c_2, c_3, \ldots, c_n$. Target application adaption parameters 505 are received, via the at least one interface 511, in order to consider that the target paint coating is to be applied on a substrate using the target paint application process. The target application adaption parameters 505 may be manually input, retrieved from a repository and/or calculated using a method as described, for example, in FIG. 1. The reflectance data of the target paint coating are computed, using the physical model 540 implemented and running on the computer processor. The predicated reflectance data 506 of the target paint coating are made available in the computer processor for further use in paint formulation calculation and/or for the development of automotive coatings and/or automotive refinish coatings. The predicted color 506 can be output via an interface 512, for example, on a display.

As already mentioned before, according to the present invention, the physical model 540 for the prediction of the reflectance properties of a paint coating (related with the reference paint application process), i.e. for the prediction of the color of the paint coating is extended with the additional application adaption module which is configured to adapt the predicted reflectance data to the given target paint application process. The additional module is configurable by input of the (target) application adaption parameters 505.

LIST OF REFERENCE SIGNS

101 samples
102 formulations of samples
103 measured colors of samples
105 application adaption parameters
110 computer processor
111 (input) interface
112 (output) interface
120 database
130 numerical optimization algorithm
140 physical model
201 target color
202 optimized target formulation
205 target application adaption parameters
206 predicted color for target application process
211 (input) interface
212 (output) interface
220 database
240 physical model
301 target color
302 optimized target formulation
305 target application adaption parameters
306 predicted color for target application process
307 true color for target application process
308 systematical bias

309 model bias
309* application process bias
310 comuter processor
311 (inut) interface
312 (output) interface
320 database
330 numerical optimization algorithm
340 physical model
401 sample coating
402 sample formulation
403 measured sample color
406 predicted sample color for target application process
410 offset
502 target formulation
505 target application adaption parameters
511 (input) interface
512 (output) interface
520 database
540 physical model

The invention claimed is:

1. A method for providing application adaption parameters to compensate for an influence of a given target paint application process on a color matching method and/or to consider an influence of a given target paint application process within a color predicting method which use a database which comprises specific optical data of individual color components, the specific optical data of the individual color components being determined on the basis of known reference paint coatings with known reference color formulations and known measured reference colors, the reference paint coatings being applied on a substrate using a reference paint application process, respectively, the method comprising:

A. applying a sample paint coating on a substrate using the given target paint application process, B. receiving, via at least one interface of at least one computer processor, data of a color formulation of the sample paint coating, C. retrieving, from the database, specific optical data of individual color components used in the color formulation of the sample paint coating, D. receiving, via the at least one interface, a measured color of the sample paint coating applied on the substrate using the given target paint application process, E. providing a numerical method and a physical model wherein the numerical method is configured to optimize application adaption parameters by minimizing a given cost function starting from a given set of initial application adaption parameters, the given cost function being particularly chosen as a color distance between the measured color and a predicted color of the sample paint coating and the physical model is configured to predict the color of the sample paint coating by using as input parameters the color formulation of the sample paint coating and the retrieved specific optical data of the individual color components used in the color formulation of the sample paint coating and respective preliminary application adaption parameters resulting in the course of optimization, and F. calculating, using the at least one computer processor and using the numerical method and the physical model implemented and running on the processor, the application adaption parameters by comparing the recursively predicted color of the sample paint coating with the measured color of the sample paint coating until the given cost function falls below a given threshold, wherein the calculated application adaption parameters are retrievably stored in a repository and assigned to the given target paint application process as process-specific application adaption parameters that can then be retrieved from the repository at any time on request.

2. The method according to claim 1 which is executed for a plurality of different given target paint application processes.

3. The method according to claim 1, wherein the given target paint application process is selected from a group of available paint application processes, each of the available paint application processes is assigned a set of process-specific application adaption parameters wherein each application adaption parameter takes into account a respective variable which changes with the respective paint application process in relation to the reference paint application process and wherein each application adaption parameter takes on a process-specific value for each of the available paint application processes.

4. The method according to claim 1, wherein each application adaption parameter is assigned to an adaption measure of a number of different adaption measures, the number of different adaption measures comprising at least one selected from the group consisting of: layer thickness adaption, adaption of effect flake orientation distribution, adaption of effectivity of solid color components, and adaption of effectivity of effect color components.

5. A computer-implemented color matching method using a color formulation calculation algorithm running on at least one computer processor and a database which comprises specific optical data of individual color components, the specific optical data of the individual color components being determined on the basis of known reference paint coatings with known reference color formulations and known measured reference colors, the reference paint coatings being applied on a substrate using a reference paint application process, for determining a target color formulation for a target paint coating which matches a given target color when being applied on a substrate using a given target paint application process, the computer-implemented color matching method comprising:

receiving, via at least one interface of the at least one computer processor, the given target color, receiving, via the at least one interface, application adaption parameters which are calculated using the method according to claim 1, wherein the calculated application adaption parameters are retrievably stored in a repository and assigned to the given target paint application process as process-specific application adaption parameters that can then be retrieved from the repository at any time on request, and calculating, using the given target color and the received application adaption parameters as input parameters for the color formulation calculation algorithm, a color formulation with optimized concentrations of individual color components as target color formulation for the target paint coating when the target paint coating is applied on a substrate using the given target paint application process.

6. The computer-implemented color matching method according to claim 5, wherein the color formulation calculation algorithm is realised by a numerical method and a physical model, wherein the numerical method is configured to optimize concentrations of individual color components of a preliminary color formulation in relation to the target color by minimizing a given cost function, starting from a given initial color formulation, the given cost function being particularly chosen as a color distance between the received target color and a predicted color of the preliminary color formulation, and the physical model is configured to predict the color of the preliminary color formulation by using as input parameters concentrations of the individual color components used in the preliminary color formulation, specific optical data of the individual color components used in the color formulation and the received application adaption parameters, and wherein the optimized concentrations of the color components are calculated by comparing the recursively predicted color of the preliminary color formulation with the target color until the given cost function falls below a given threshold.

7. A computer-implemented method for predicting, using a color predicting physical model running on at least one computer processor and a database which comprises specific optical data of individual color components, the specific optical data of the individual color components being determined on the basis of known reference paint coatings with known reference color formulations and known measured reference colors, the reference paint coatings being applied on a substrate using a reference paint application process, reflectance data of a target paint coating, wherein the target paint coating is to be applied on a substrate using a given target paint application process, the computer-implemented method comprising:

a. receiving, via at least one interface of the at least one computer processor, data of a color formulation of the target paint coating, b. retrieving, from the database, specific optical data of individual color components used in the color formulation of the target paint coating, c. receiving, via the at least one interface, application adaption parameters, the application adaption parameters being calculated according to the method according to claim 1, wherein the calculated application adaption parameters are retrievably stored in a repository and assigned to the given target paint application process as process-specific application adaption parameters that can then be retrieved from the repository at any time on request, and d. calculating the reflectance data of the target paint coating using the physical model implemented and running on the at least one computer processor, wherein the received data of the color formulation of the target paint coating, the retrieved specific optical data of the individual color components used in the color formulation and the received application adaption parameters are entered into the physical model as input parameters, and making the predicated reflectance data of the target paint coating available in the at least one computer processor for further use in paint formulation calculation and/or for the development of automotive coatings and/or automotive refinish coatings.

8. A computer-implemented method for color simulation for an available paint application process, using a color simulation algorithm running on at least one computer processor and a database which comprises specific optical data of individual color components, the specific optical data of the individual color components being determined on the basis of known reference paint coatings with known reference color formulations and known measured reference colors, the reference paint coatings being applied on a substrate using a reference paint application process, for determining whether a given target color of a target paint coating is producible with the available paint application process, the computer-implemented method comprising:

receiving, via at least one interface of the at least one computer processor, the given target color, retrieving, from the database, specific optical data of individual color components used in a color formulation of the target paint coating, receiving, via the at least one interface, application adaption parameters for the available paint application process, which are calculated using the method according to claim 1, wherein the calculated application adaption parameters are retrievably stored in a repository and assigned to the given target paint application process as process-specific application adaption parameters that can then be retrieved from the repository at any time on request, calculating, using the retrieved specific optical data of the individual color components used in the color formulation of the target paint coating and the received application adaption parameters as input parameters for the color simulation algorithm, a color formulation with optimized concentrations of the individual color components with respect to the target color, and predicting a color associated with the calculated color formulation when a respective paint coating of the calculated color formulation is applied on a substrate using the available paint application process, comparing the predicted color with the target color, particularly by determining a color distance, and indicating that the target color is producible with the available paint application process if a difference between the predicted color and the target color is within a given tolerance range.

9. A system, comprising at least:

a database which comprises individual color components and specific optical data associated with the respective individual color components, the specific optical data of the individual color components being determined on the basis of known reference paint coatings with known reference color formulations and known measured reference colors, the reference paint coatings being applied to a substrate using a reference paint application process, respectively, and at least one computer processor, which is in communicative connection with the database, and programmed to execute the method according to claim 1.

10. A non-transitory computer readable medium with a computer program with program codes that are configured and programmed, when the computer program is loaded and executed by at least one computer processor which is in communicative connection with a database which comprises individual color components and specific optical data associated with the respective individual color components, the specific optical data of the individual color components being determined on the basis of known reference paint coatings with known reference color formulations and known measured reference colors, the reference paint coatings being applied to a substrate using a reference paint application process, respectively, to execute the method according to claim 1.

11. The computer-implemented method according to claim 8, wherein the difference between the predicted color and the target color is a color distance.

12. The system according to claim 9, wherein the individual color components comprise pigments and/or pigment classes.

13. The non-transitory computer readable medium according to claim 10, wherein the individual color components comprise pigments and/or pigment classes.

\* \* \* \* \*